us010430626B2

(12) United States Patent
Richter

(10) Patent No.: US 10,430,626 B2
(45) Date of Patent: Oct. 1, 2019

(54) CARRIER FOR THE EXAMINATION OF WORKPIECES BY COMPUTED TOMOGRAPHY

(71) Applicant: Carl ZEISS 3D Automation GmbH, Aalen (DE)

(72) Inventor: Frank Richter, Heidenheim (DE)

(73) Assignee: CARL ZEISS 3D AUTOMATION GMBH, Aalen (DE)

( * ) Notice: Subject to any disclaimer, the term of this patent is extended or adjusted under 35 U.S.C. 154(b) by 273 days.

(21) Appl. No.: 15/631,193

(22) Filed: Jun. 23, 2017

(65) Prior Publication Data
US 2017/0372099 A1 Dec. 28, 2017

(30) Foreign Application Priority Data

Jun. 23, 2016 (DE) ................... 10 2016 211 294

(51) Int. Cl.
*A61B 6/00* (2006.01)
*G06K 7/10* (2006.01)
*G01N 23/046* (2018.01)
*G06K 19/06* (2006.01)

(52) U.S. Cl.
CPC ......... *G06K 7/1099* (2013.01); *G01N 23/046* (2013.01); *G06K 19/06037* (2013.01); *G01N 2223/307* (2013.01)

(58) Field of Classification Search
CPC ........... G06K 7/1099; G06K 19/06037; G01N 23/046; G01N 2223/307
See application file for complete search history.

(56) References Cited

U.S. PATENT DOCUMENTS

| 6,584,214 | B1 * | 6/2003 | Pappu | G06K 9/00 340/5.86 |
| 6,899,275 | B2 | 5/2005 | Schramm | |
| 8,897,534 | B2 * | 11/2014 | Oeckl | G06T 7/70 382/132 |
| 9,025,855 | B1 * | 5/2015 | Christoph | G01N 23/046 382/152 |
| 10,132,762 | B2 * | 11/2018 | Beckett | G01N 23/18 |

FOREIGN PATENT DOCUMENTS

| EP | 2587450 A1 | 1/2013 |
| JP | 02003881 A | 9/1990 |

* cited by examiner

*Primary Examiner* — Kiho Kim
(74) *Attorney, Agent, or Firm* — Norton Rose Fulbright LLC

(57) ABSTRACT

A workpiece having an identification code is arranged on a workpiece carrier having coded therein, by a pattern made from a plurality of mutually separate regions of different density, at least one character of the identification code. The workpiece and carrier are scanned together by computed tomography, the regions or part of the regions and the densities thereof in the computed tomography scan are ascertained, the scan is oriented in response to at least the location of a straight line through two of these regions, the character that is coded by way of the density pattern of the plurality of regions is determined in the scan, and the oriented scan is processed in response to the coded character.

21 Claims, 2 Drawing Sheets

CARRIER FOR THE EXAMINATION OF WORKPIECES BY COMPUTED TOMOGRAPHY

CROSS-REFERENCE TO RELATED APPLICATION

The present application claims priority under 35 U.S.C. § 119 to DE 10 2016 211 294.5, filed in the Federal Republic of Germany on Jun. 23, 2016 and the content of which is incorporated herein by reference in its entirety.

FIELD OF THE INVENTION

The present invention relates to the examination of workpieces.

BACKGROUND

In many areas of production, it is vital that prescribed specifications of individual workpieces that will be assembled to form a larger product be observed. This necessitates that measurements and tests on workpieces are carried out, i.e., that they are examined. This is true even where a multiplicity of different workpieces must be examined such as during the manufacturing of very small batches or of highly complex apparatuses containing a large number of different elements, and often the examination must be performed quickly.

One possible examination method for typical measurement and test tasks is computed tomography (CT). CT images of workpieces permit a comparison between an actual shape thereof and a desired shape thereof and possibly also grant the ability to detect internal defects of a workpiece, such as shrinking holes inside the body and the like. However, as CT scanners are expensive, it is desirable to, as much as possible, reduce the time required to take an image of a workpiece using a CT scanner, in particular during manufacturing.

It has been suggested to transport workpieces on a carrier into the examination space of industrial CT scanners. Such carriers can be arranged as pallet systems or pallet stacks that are placed on a movable table inside the examination space. It may be possible in this case to arrange a plurality of parts next to one another or on top of one another, move them together into the industrial CT scanner, and finally successively prepare CT images of the individual workpieces inside the machine by moving a table, e.g., in the z-axis.

Although changeover times are reduced in this manner and although it becomes possible to examine different workpieces in quick succession using a CT scanner, not only must it be ensured that the examination results relating to the workpieces to be examined become available in short order, but it must also be ensured that the examination results are accurate enough and that they are correctly assigned.

This is important in particular where the production parameters of a current production process might need to be adapted on the basis of a measurement or test result.

It has already been suggested to identify the individual pallets of a pallet stack and different workpiece positions on a palette by way of suitable codes. Optically readable line codes or matrix codes, e.g., barcodes or QR codes, have already been used for this purpose. RFID chips that are readable by way of radio waves and the like have also already been used.

Another suggestion in the past has been to provide X-ray recordings and the like with blocks of varying density which together are intended to code characters and are photoelectrically readable from X-ray images, cf. JP 0 200 3881 A.

Another suggestion has been to generate a machine-readable mark from a multiplicity of labels arranged one on top of another, cf. U.S. Pat. No. 6,899,275 B2. One complete symbol can thus be coded in each layer or be divided into fragments that are distributed over a plurality of layers. Said document also discusses reading the machine-readable mark using ultrasound or X-ray techniques, among others.

EP 2 587 450 A1 discloses the use of positioning marks to be used to scale, rotate, dewarp, etc. X-ray recordings or tomographic recordings. It has been suggested to use marks in non-symmetrical form to reduce rotation errors and to provide clearly discernible shapes in an image. It has been suggested that a material that has been adapted to the X-rays of the corresponding energy is used in a size that is adapted to the image field, for example a diameter of 100 µm to 0.8 mm.

SUMMARY

It is desirable to ensure robust and error-free processes in industrial manufacturing, especially where a multiplicity of different products are to be examined quickly and accurately under great time pressure.

An object of the present invention is to provide innovations for industrial application.

An example embodiment of the present invention is directed to an examination method in which a workpiece having an identification pattern is recorded by way of computed tomography. A workpiece carrier is provided with at least one pattern by way of which, using a multiplicity of separated regions having densities that contrast with their environment, a character of an identification code is coded. The workpiece is arranged on the carrier, the workpiece and the carrier are together recorded by way of computed tomography, the regions and the densities thereof in the computed tomography recordings (CT recordings) are ascertained, the recordings are oriented in response to at least the orientation of one straight line through two regions, the character that is coded by way of the density pattern of the multiplicity of regions in the recording is determined, and then the oriented recordings are further processed in response to the coded character. Note that the coded character or "symbol" can have more than one digit depending on the code employed.

The only requirement is thus to initially find an easily identifiable code character in the CT recording. This can be done particularly quickly because the workpiece carrier is typically formed with surfaces that are largely standardized and homogeneous in themselves, for example having a base surface with which the carrier is placed on a displaceable or otherwise movable measurement table in the CT scanner. As a result, no separate sensors for capturing carriers or codes are necessary and assignment between code and CT recording is possible without errors or mixups. In addition, the volume of the CT scanner that is to be taken into consideration initially is relatively small, so that it is possible from the start to take into consideration only a small fraction of the entire recorded computed tomography voxels on the basis of the recording itself.

Since the density of the regions contrasts with their environment, it is particularly easy to identify the regions in the small volume that is to be examined in the first place, for example by way of a simple threshold comparison. Density here is understood to mean the X-ray density, i.e., a great density is assumed if the material is opaque to X-rays, and a low density is assumed if the material is highly transparent to X-rays.

After a first, very fast step, it is then possible without further ado to decode the density pattern and then, on the basis of the density pattern, to automatically determine the further processing of the CT recording. Since at the same time orientation of the recording has already been completed, the further processing of the oriented recording can likewise be effected particularly quickly. It should be noted that a much faster evaluation of the recording can be performed even if the orientation is only a rough one, i.e., is inaccurate. Orientation can be performed by way of a simple conversion of coordinates, and great accuracy may not even be necessary here.

It is possible to ensure based on the evaluation that the selected processing corresponds exactly to the processing that is necessary according to the identification code for a respective specific workpiece; for example, it is possible to begin a measurement of the total volume, of the shape accuracy etc. immediately for the right workpiece, without having to worry about errors in assignment and the like. The examination of the CT recording can also omit all voxels in which no parts of the workpiece are expected to be present. Examining the CT recording can thus be limited to a "layer" around the workpiece if only surface measurements, such as for example for determining the dimensional accuracy, are required, or said examination can take into consideration all voxels located within a corresponding volume. In the case of a workpiece carrier which itself is provided with the identification code, the robustness of the code pattern that is required for industrial processes is also provided without making any special effort because the corresponding minimum regions can be arranged easily inside the carrier body where they are protected.

For the simplification of the evaluation it is particularly preferred for the method if the coding regions have a geometrically simple shape.

Particularly preferred shapes here are spheres or cubes. A spherical shape is advantageous because it permits simple determination of the centroid independently of the alignment of the carrier body. The cube shape is advantageous where the intention is to examine a well-aligned recording particularly quickly. For determining the cube areas, only a number of voxels need to be read from a memory and a threshold comparison be carried out, if appropriate. In the case of a cube shape, reading can be particularly easy.

Instead of cubes, long, stretched cuboids can be used and/or cuboids can be assembled from a plurality of cubes, in particular cubes of varying densities in order to define different regions one directly next to another, which together code the character or are used together in character coding, possibly with other regions which are spatially separate.

Such assembled cuboids can have regions of varying densities that contrast with the cuboid environment and/or that code, by their total size, a character, where, in particular, a plurality of elements of identical densities contribute to the coding.

It is possible in the same way to use spheres of different sizes for the coding, where the spheres can additionally have different density values that contrast with the environment. It is in particular possible in the case of a mid-range density of the environment, for example if the carrier body has a mid-range density, to configure regions to be hollow or foamed and thus as having a low density, and also to form coding regions that are particularly opaque to X-rays.

It is advantageous and preferred if provision is made in an examination method for a desired location of the at least two regions to be at least approximately known and for positioning to be effected on that basis.

It is possible by way of the initial search in specified regions in a newly recorded CT image, for which no decoded patterns have yet been identified, to simplify the evaluation significantly if the examination method is carried out using a carrier in which the desired location of the coding regions or parts of the coding regions is at least approximately known. It is preferred in particular if the examination method is performed with a generally planar carrier and the location of the regions relative to the plane is known. For example, in one preferred variant, the regions are arranged centrally within the carrier plate volume. The initial search for a carrier plate is therefore restricted to the vicinity of the plate of a displaceable table and to capturing therein strongly contrasting regions at a given height. As is clear, this can be performed quickly and with precision.

It is advantageous and preferred if provision is made in an examination method for the CT image to be recorded with a dynamic of at least three distinguishable density levels and for the code to comprise characters that are coded in non-binary fashion at least in one region. It is thus possible to provide regions that are strongly opaque to X-rays, but where the X-ray opacity of the regions differs identifiably (among one another or separately), and/or it is possible to provide, for example, both cavities having a particularly low X-ray opacity in the carrier body and also volumes with a foam-like or mesh-like structure within an otherwise dense carrier body for coding the regions. Since only an average density of the regions needs to be captured, a correspondingly formed region will differ clearly from a completely empty one and from a region provided with a material that is opaque to X-rays or an environment.

This permits coding of characters not only in merely binary fashion, which reduces the required number of regions or increases the number of distinguishable characters coded by a given number of regions.

While it is possible in principle to locate the strongly contrasting regions at an arbitrary location, in particular if, for example, only the coded regions have a particularly high X-ray opacity or the like, it is generally preferred to provide a specific number of standardized regions on the carrier in which the density is determined in each case. As a result, the quantity of voxels to be evaluated initially in particular can be reduced and thus the time for the evaluation of an image can be decreased significantly, while reducing the risk of erroneous determinations at the same time.

In a particularly preferred variant, the examination method is performed such that the workpiece carrier comprises at least one base plate, and initially a search is carried out for characters coded in the base plate. It is then possible to ascertain on the basis of a character that is present in the base plate if further locations should be searched for coded characters, for example because a plurality of planes are present or because the base plate code indicates that the base plate comprises a carrier that is adapted to a workpiece contour. It is here possible, if appropriate, for clues to be given to further locations that are to be searched for a code, e.g., specific column positions or at a given height within a contoured workpiece carrier.

In a particularly preferred variant, what is examined in the examination method is where within the region the centroid is located, i.e., for example the contrast edges with the environment are ascertained and then the centroid for the volume located inside said contrast edges is determined. It is possible here for the X-ray opacity of the individual voxels to be taken into consideration; however, this is not absolutely necessary, if appropriate. If the density values obtained at individual voxels are not taken into consideration, the result is a centroid that is located purely geometrically between the contrast edges.

It is possible to search a database for a corresponding data processing method in response to a captured pattern or the correspondingly decoded character, and to then process the CT recording further in accordance with the data processing method that has been respectively ascertained and retrieved from the database. For example, it is possible for the comparison with a specific workpiece, for example either a cylinder piston, a connecting rod or an engine block to be prescribed and for the respective desired dimensions and contours to be retrieved for the comparison.

Since the recording is aligned in accordance with the invention, it is then also possible to ascertain where (approximately) the comparison body will be located, with the result that the desired/actual comparison with an identified desired workpiece can be performed particularly quickly.

It is advantageous and preferred if provision is made in an examination method for the carrier to have standardized regions in which the density is determined.

It is advantageous and preferred if provision is made in an examination method for the workpiece carrier to comprise at least one base plate and for a determination to be made in response to a character that is coded in the base plate as to whether a plurality of planes are present and/or whether a search for density variations should be carried out at sites where columns between pallet planes are provided in pallet stacks.

It is advantageous and preferred if provision is made in an examination method for the location of the centroid in the regions to be determined and used for the orientation.

It is advantageous and preferred if in an examination method a data processing method is selected from a number of possible data processing methods in a database in response to the decoded character and the corresponding CT recording is then further processed according to the selected data processing specification, where the data processing selection preferably also comprises the determination of volumes of the CT scanner for the examination.

An example embodiment of the present invention is directed to a carrier for workpieces to be examined by computed tomography, where the carrier includes a carrier body and a pattern formed from a multiplicity of regions, which pattern uniquely codes an identification symbol, where the multiplicity of regions comprise mutually separate volumes on the carrier body, where the density values averaged over the volumes are selected such that they form the pattern that uniquely codes the identification symbol, and where at least two selected regions of the multiplicity of regions are spaced apart from each other or stretched at least far enough for all straight lines that extend through at least in each case 1 voxel of both regions to intersect at an angle of no more than 10°, preferably 5°, with particular preference 1°, and/or for one straight line through the centroid of the regions relative to the carrier to be fixed with an accuracy of better than 5°, preferably 1°, and these regions have averaged CT density values that contrast with the density of the carrier body environment thereof that has been determined by computed tomography.

In view of what was just said, it will be appreciated that such a carrier can be used to particularly easily perform an examination method that is suitable for the quick examination of a multiplicity of different interchanging workpieces by way of computed tomography.

It is advantageous and preferred if in a carrier at least three selected regions of the multiplicity of regions have averaged CT density values that contrast with the density of the adjoining carrier body as determined by computed tomography and are arranged such that one of these three regions is not located on a straight line running through the other two of the three regions, wherein the volume centroids of the three regions preferably form a triangle, with each angle being at least 15°, with particular preference at least 30°.

This arrangement is advantageous because the regions are more clearly separated thereby and are generally located on the carrier over greater distances from one another, which is advantageous for the measurement accuracy. The alignment can be effected more accurately.

The volumes can be completely solidly enclosed inside the carrier body volume or be partially solidly enclosed. The complete enclosure in the carrier body material contributes to a particularly great robustness. If volumes are only partially enclosed, for example because they are incorporated in depressions on the carrier body surface, quick placement and changing of the code characters can be achieved. This can likewise have advantages, in particular if longer codes are to be used and a carrier is to be manually provided in each case with such a code.

From what was said above it can be gathered that the examination methods disclosed are applicable in particular where the carrier body has a planar surface such as a pallet or a base plate. For this reason, the carrier will preferably comprise at least one pallet as the carrier body, where the regions will typically be arranged near or on the center of the thickness of the base surface.

If a plurality of small workpieces are to be examined in quick succession, it may be advantageous for them to be arranged on a pallet stack or the like and to be introduced together with it into the measurement space of a CT scanner. Where such pallet stacks are possibly used, it may be advantageous to code the number of the planes or to code, for example starting from the base plane, whether another plane is present. This can be the case for a pallet stack within the individual planes and/or when arranging regions in columns.

It is thus initially possible to determine in each case by way of a suitable code character whether further characters are present, possibly where a search for them should take place, and to only then perform the actual workpiece examination on the basis of the (reduced number of) voxels (to be taken into consideration).

If a voluminous, non-flat body is used as the carrier, for example one that is adapted to a workpiece contour, it will be advantageous for the regions that are part of the pattern to be arranged neither in collinear nor coplanar fashion and to code a workpiece that is to be placed on it. It is thus possible for an alignment of the CT image to be effected by way of pivoting, swiveling and tilting and also by way of translational movement, and also a selection of the voxels that are actually to be taken into consideration in a large recorded CT image.

In a particularly preferred variant, the entire carrier or carrier body or part thereof can be produced using 3D printing. In the case of three-dimensional printing, it is possible to produce regions that are particularly opaque to X-rays by way of changing the print-technological parameters, by way of incorporating a special material, and/or by leaving regions free. It is thus easily and quickly possible to provide a carrier having a coding pattern without any special effort.

The volumes of the regions inside the carrier with which coding is effected will preferably comprise at least 5×5×5 voxels, preferably with voxel sizes of >3 mm×3 mm×3 mm, particularly preferably with voxel sizes of >6 mm×6 mm×6 mm. In a particularly preferred variant, the volumes will be even larger. A sufficient number of voxels per region ensures that, where voxels on the volume surfaces are only partially filled with the contrasting material, edge effects or boundary surface effects will be less pronounced.

It is advantageous and preferred in a carrier if provision is made for the volumes of all selected regions to be at least partially solidly enclosed within the carrier body volume, preferably completely enclosed.

It is advantageous and preferred if provision is made in a carrier for said carrier to comprise at least one pallet as the carrier body, preferably at least one pallet having regions that are arranged near or on the center of the thickness of its base surface.

It may be advantageous and preferred if the carrier comprises at least one pallet stack having at least one pallet as the carrier body, where preferably each pallet of the stack is coded by the pattern to at least indicate whether a further plane is present and/or where the carrier body comprises columns that are provided with regions associated with the pattern.

In an example embodiment, the carrier advantageously comprises a body that is adapted to a workpiece contour, preferably a body adapted to a workpiece contour in which the regions associated with the pattern code a workpiece that is to be placed on it and are neither collinear nor coplanar.

According to an advantageous example embodiment, at least the part of the carrier body that is provided with the pattern made from a multiplicity of regions is produced by way of three-dimensional printing, preferably a three-dimensional printed structure in which the regions are left free and/or which has foam-like cavities, and/or in which the density is increased by inserting third bodies and/or by print-technological means, in particular by changing the printing parameters and/or with material.

An example embodiment of the present invention is directed to a carrier for workpieces to be examined by computed tomography, the carrier having a carrier body and a multiplicity of regions that are fixedly arranged at positions that are distributed over the carrier body and are spaced apart from each other, where at least three regions of the multiplicity of regions have averaged CT density values that contrast with the density of the carrier body surrounding it as determined by computed tomography and are arranged such that one of these three regions is not located on a straight line running through the other two of the three regions, where the regions have averaged density values, which are arranged in a pattern and together uniquely code an identification symbol.

The invention will be described below, by way of example, with reference to the drawings.

DETAILED DESCRIPTION

Figure 1:
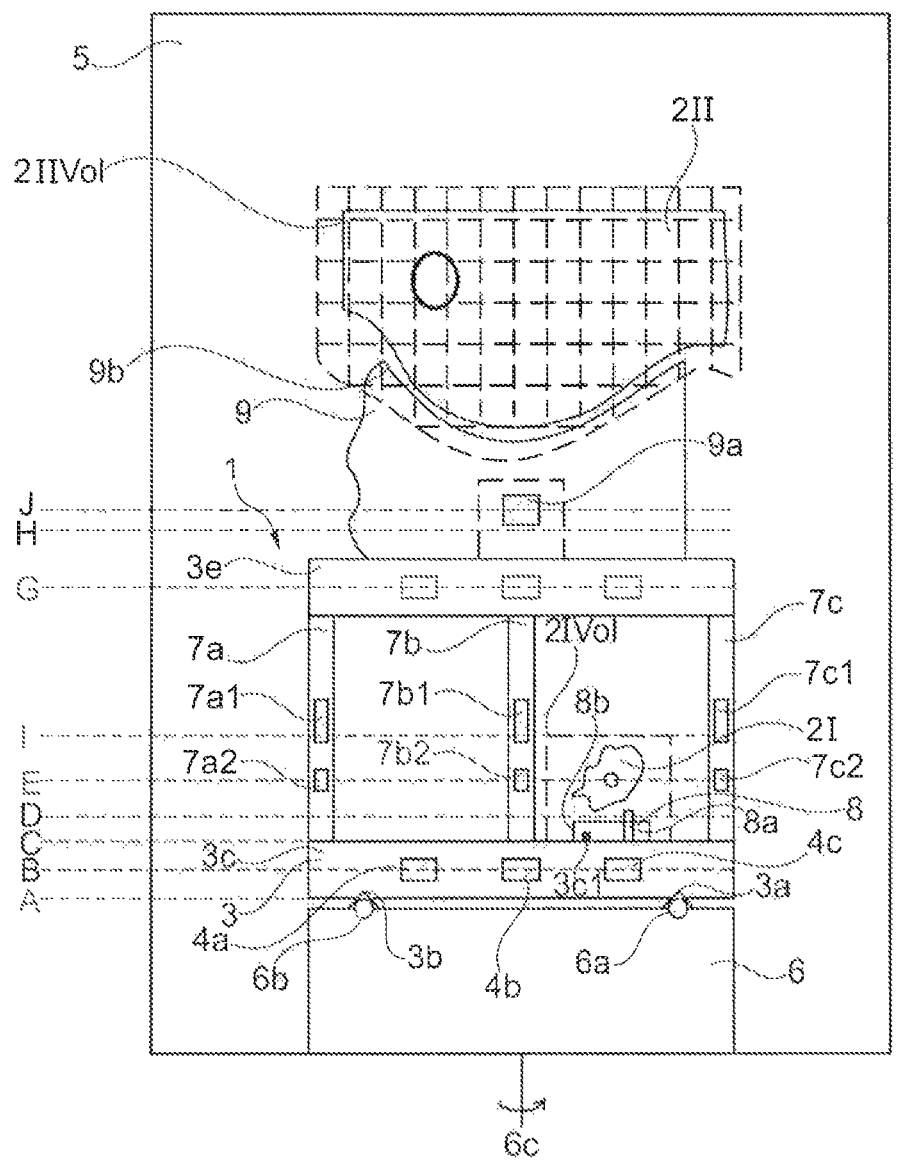
FIG. 1 illustrates a carrier for workpieces to be examined by computed tomography, according to an example embodiment of the present invention.

FIG. 1 shows a carrier 1 for workpieces 2I, 2II that are to be examined by computed tomography. Carrier 1 includes a carrier body 3 and a pattern formed from a multiplicity of regions 4a, 4b, 4c that comprise volumes on the carrier body, where density values averaged over the volumes are selected such that they form a pattern that uniquely codes an identification symbol. At least two selected regions 4a, 4b, cf. FIG. 2, are spaced apart from each other and extend far enough for all straight lines, cf. e.g., g1 and g2, that extend through voxels of both regions to intersect at an angle of no more than 10°, and/or one straight line through the centroid, illustrated by the centroid 4cs for the region 4c and the centroid 4as for the region 4a, relative to the carrier is fixed with an accuracy of better than 5°, preferably 1°, where these regions have averaged CT density values that contrast with the density of the carrier body environment thereof that has been determined by computed tomography.

In the present method, the carrier 1 serves for bringing a plurality of workpieces 2I, 2II into the measurement space 5 of a CT scanner in which the carrier 3 is arranged on a measurement table 6. In the exemplary embodiment that is illustrated, the measurement table is provided with fit elements 6a, 6b which mate with contours 3a, 3b shaped in complementary fashion in the carrier body base plate 3c of the carrier body 3 such that a carrier body can always be placed at the same site onto the measurement table. The measurement table is pivotable about an axis 6c and otherwise movable as required in order to capture objects located in the measurement space by computed tomography.

Figure 4:
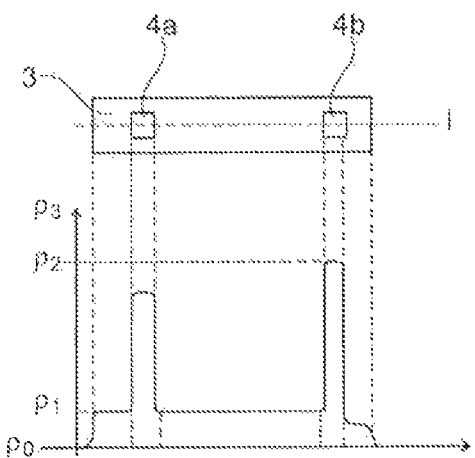
FIG. 4 is an example density histogram through two regions 4a, 4b of a carrier body 3, according to an example embodiment of the present invention.

The base plate is manufactured from plastic using a 3D printing method and has a low X-ray density. Incorporated therein are the regions 4a, 4b, 4c made of material having a higher X-ray density. These are formed by further introduction of different materials into the volume of the carrier body 3 during 3D printing. At the sites of the regions 4a, 4b, 4c, the X-ray density is here significantly greater, as is indicated along a line L in FIG. 4 by way of the X-ray optical density profile. It can be seen here that the X-ray density of the base body 3 is only slightly greater than that of the surrounding air, cf. ρ compared to ρ0, but also that in the regions 4a and 4b the X-ray density increases to a value ρ2 that relates to a multiple of the value of ρ1. While in the illustrated exemplary embodiment the density within the regions 4a, 4b is homogeneous, this does not necessarily have to be the case, and it is also possible for regions of different densities to be provided that nevertheless contrast with the density of the environment ρ1. In addition to the pattern points 4a, 4b, 4c arranged in the present case in an equilateral triangle, further regions 4d1, 4d2, 4d3 are provided near the centroid of said triangle that code a character here together with the regions 4a, 4b, 4c. Provided in the carrier body base plate 3c are furthermore attachment points 3d1, 3d2, 3d3 for columns 7a, 7b, 7c that carry a second plate 3e which likewise belongs to the carrier 3. Also incorporated in the columns 7a, 7b, 7c are regions, cf. 7a1, 7a2, 7b1 7b2, 7c1 7c2, which together code information and are located at a fixed height within the columns and in the volumes thereof.

Figure 2:
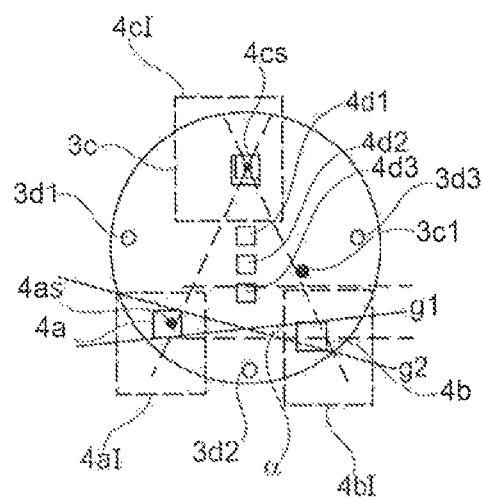
FIG. 2 shows a section through a first carrier plate for a carrier in accordance with FIG. 1, according to an example embodiment of the present invention.

Provided on the lower carrier body 3c is a workpiece carrier 8 which is fixed at a desired position 3c1, cf. FIG. 2, and has in its interior a region having an X-ray density 8a, which contrasts with the surrounding carrier, at a predefined site, where the X-ray density thereof is selected such that the workpiece 2I, which is located on the surface 8b of the carrier 8, which surface is contoured in complementary fashion therewith, is identifiable on the basis of the X-ray density. The X-ray density in carriers for different workpieces can thus be different for different workpieces.

The regions 7a1, 7a2, 7b1, 7b2, 7c1, 7c2 code the length of the columns 7a, 7b, 7c.

Provided on the carrier 3e is a carrier body 9 having a region of contrasting X-ray density 9a in order to code which workpiece 2II is arranged on the contoured surface 9b of the carrier body 9.

The CT scanner is configured to be able to completely measure all the workpieces that are able to be brought into the region 5, and the measurement table 6 can be moved correspondingly to this end. During the measurement, a multiplicity of voxels are recorded, comparable to the pixels of a two-dimensional image.

Figure 3:
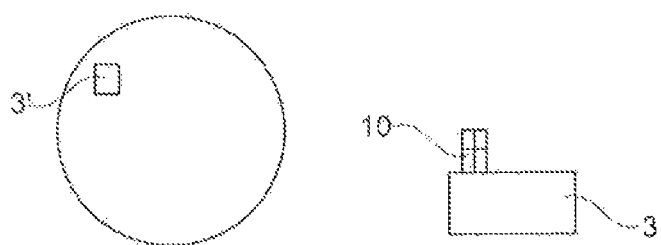
FIG. 3 represents a carrier according to an alternative example embodiment of the present invention.

One alternative to a pattern that is incorporated in a body, such as a carrier body, made of regions of contrasting X-ray optical density is illustrated in FIG. 3. Here, a carrier body 3' is provided with a region 10 which is arranged directly on the carrier body and is made up of a multiplicity of different material blocks having different X-ray opacities. This allows the definition of carriers that are identifiable ad hoc without previous three-dimensional printing of carrier bodies, where these can have fixed regions.

It will be appreciated from what was just said that the patterns provided on the carrier body are able to code a character from a plurality of predefined characters and that decoding the patterns necessitates the determination of the densities, i.e., the X-ray densities, of the individual regions. At least in patterns such as that of the equilateral triangle 4a, 4b, 4c it is advantageous to make decoding independent of the alignment of the carrier. Where, for example, two of the regions 4a, 4b, 4c have a density $\rho 2$ in FIG. 4 and one of the regions has a density $\rho 3$, for example it is preferred if a code $\rho 2$, $\rho 2$, $\rho 3$ codes the same character as a code $\rho 3$, $\rho 2$, $\rho 2$ or $\rho 2$, $\rho 3$, $\rho 2$, so that what needs to be done is just to notice that the optical densities $\rho 2$ and $\rho 3$ differ from one another and that they differ from the environment having the density $\rho 1$.

According to an example embodiment of the present invention, a database (not illustrated), in which the different characters are associated with the densities, also stores which further processing of a CT recording is to be effected. In the present case, for example, the pattern in the carrier body base plate 3c codes that a carrier body 8 is arranged on the carrier body base plate and that the carrier body base plate 3c carries three columns. The pattern in the columns 7a, 7b, 7c codes how long the columns are; the region 8a codes that a workpiece 2I is to be examined, and the pattern in the plate 3e codes that no further columns are present and a carrier body 9 for a workpiece is provided. The pattern in the region 9a codes that a workpiece 2II is to be examined. It should be noted that the regions 9a and 8a can be formed in carrier bodies from a multiplicity of adjacent, varying regions having varying densities that contrast with the environment. It should be noted that it is possible for a CT scan evaluation unit, for example a computer, to be used to access the corresponding database. The association between patterns and meaning of the coding can be effected by way of letters or numbers, such as "1", "2", "3" etc. However, the direct reference to a database or in a database is also understood to be a symbol or character in accordance with the patent.

The arrangement is used to examine workpieces as follows. Initially, the pallet stack is constructed from a carrier body base plate 3c, a base plate 3e, and columns 7a, 7b, 7c each being provided with the respective coding regions. Next, the carrier bodies 8 and 9 are placed at their given sites onto the base plates 3c and 3e, respectively. Workpieces 2I and 2II to be examined can now be placed onto the respective contour and thus in aligned fashion. The pallet having the two workpieces is placed, according to the contour pairs 6a/3a and 6b/3b, at the desired position on the measurement table 6, and measurement is started.

In a first exemplary embodiment of the invention, the measurement space is measured in its entirety, i.e., the X-ray density of each reachable voxel is captured. In other words, a CT image that captures the total volume of the measurement space is established, specifically having gray levels that correspond to the X-ray density at a given voxel. Once the coding regions have been identified—which requires a minimum processing effort—the data can be processed easily.

Now, assume that by examining the workpieces 2I and 2II, it should now be checked whether the workpieces are dimensionally accurate, i.e., correspond to a specific desired contour. Assume that if dimensional deviations are observed, production methods during operation should be adapted as quickly as possible on the basis of this examination.

To this end, the procedure is as follows. First, the X-ray densities parallel to the measurement table are determined in the planes A, B, C, cf. FIG. 1, closely above the lowermost position of the measurement table. Since the X-ray density is determined in a plurality of planes which are slightly spaced apart, the measurement bodies and the carrier bodies do not need to be manufactured exactly with absolute precision to find the pattern from the regions 4a, 4b, 4c.

In the case of the embodiment shown, the search for the regions 4a, 4b, 4c is effected in planes A, B, C. Since the base body 3 is aligned roughly with the measurement table 6 and owing to the pairs 6b/3b 6a/3a, there is no need to search through the entire plane, and it suffices to search within a specific region, indicated in FIG. 2 by way of the dash-dotted lines 4aI, 4bI, 4cI. Since here larger regions having the values $\rho 2$ and $\rho 3$ were found and because it is possible to exclude, owing to the size of the regions, that individual voxels exhibit excessive noise, a clear pattern can be assumed, so that it is possible to determine on the basis of the densities $\rho 2$ and $\rho 3$ at the sites 4a, 4b, 4c, by referring to a corresponding database entry, that a search in a plane D should be effected as the next examination step in order to ascertain which workpiece carrier is provided on the base plate 3. By identifying the pattern in the region 8a it is possible to determine that the next pattern that is to be examined is a pattern in the region 2I-Vol.

The recording can then be aligned such that the three straight lines that run through pairs of the centroids 4as, 4bs, 4cs have a fixed spatial location relative to the measurement space. The recording is thus oriented in accordance with the pattern from the points 4a, 4b, 4c, more specifically in response to the location thereof in the CT image. It is then possible to further evaluate the pattern points 4d1, 4d2, 4d3.

Due to the alignment, the volume 2IVol can then be determined exactly.

It is then possible to carry out in the planes E and I a search, more precisely in the regions 7a1, 7a2, 7b1, 7b2 and 7c1, 7c2, which code how long the columns 7a, 7b, 7c are, i.e., where the plate 3e lies relative to the lower carrier plate and thus relative to the measurement table, and which code whether further levels are present in the carrier body pallet stack. According to the pattern from the regions 7a1 to 7c2, a search is then performed at a height G to identify the regions there that indicate that a carrier body 9 is provided and indicate in which region the pattern 9a can be found such that it is necessary to search for the region 9a only in two planes H and J. The pattern in the region 9a decodes a symbol that indicates that a search is to be carried out in a database for a method of examining a workpiece 2II, where the corresponding examination method indicates which voxels 2II are to be examined to determine the contour of the workpiece 2II in terms of dimensional accuracy by comparing it to a desired contour.

By considering a few planes and a (generally single) alignment, it is thus possible to reduce the total volume of the measurement space for examining the two workpieces to two small volumes 2IVol and 2IIVol, in which additionally the actual location of a respective workpiece is known at least approximately and where moreover it is discernible exactly from the tomographic image which workpieces are to be examined, specifically on the basis of the coded characters or symbols or the decodable patterns. For the examination of the workpieces for dimensional accuracy, it is now only necessary to search for density steps or edges in a respectively small volume and it is possible to effect further corrections, for example minor erroneous positioning, minor angle errors etc., if necessary in this small volume in order to provide a precise measurement result.

The entire examination method can thus be effected automatically once the definitions required for specific workpieces have been prescribed, without errors due to incorrect designations of workpieces occurring and the like. The evaluation is so fast that it is possible during operation to quickly make statements relating to dimensional accuracy without extensive calculations being necessary. Even where, owing to rough working handling, great wear of the carriers and the like, the soiling thereof etc. is to be expected, the reliable identification of the workpieces to be examined will easily be possible.

What is claimed is:

1. An examination method comprising:
scanning, by a computed tomography scanner, a workpiece carrier and a workpiece arranged on the workpiece carrier together by computed tomography (CT) to produce a CT scan, wherein the workpiece is assigned an identification code and the workpiece carrier is coded, by a pattern made from a plurality of separate regions of different densities, with at least one character of the identification code;
identifying in the CT scan, by an evaluation unit, the regions or a part of the regions;
identifying, by the evaluation unit, the respective densities of the identified regions or part of the regions based on the CT scan;
orienting, by the evaluation unit, the scan based on a location of a straight line through two of the identified regions;
determining, by the evaluation unit and based on a pattern of the identified densities, the at least one character; and
processing, by the evaluation unit, the oriented scan based on the determined at least one character.

2. The examination method of claim 1, wherein locations of the at least two regions is predefined and the carrier is positioned for the at least two regions to be at the predefined locations.

3. The examination method of claim 1, wherein the CT scan is recorded with a dynamic of at least three distinguishable density levels and the code includes a character that is coded in non-binary fashion at least in one region.

4. The examination method of claim 1, wherein standardized regions of the carrier, in which the density is determined, are recorded.

5. The examination method of claim 1, wherein:
the workpiece carrier includes at least one base plate;
the processing includes determining, based on a character that is coded in the base plate, at least one of whether a plurality of planes are present and whether a search for density variations should be carried out at sites where columns between pallet planes are provided in pallet stacks.

6. The examination method of claim 1, wherein a location of a centroid is determined in the regions and is used for the orientation.

7. The examination method of claim 1, wherein one of a plurality of data processing methods in a database is ascertained based on the decoded pattern and the processing is performed according to the ascertained data processing method.

8. The examination method of claim 7, wherein the ascertained data processing method identifying select volumes of the scan to be processed.

9. A carrier for workpieces to be examined by way of computed tomography, the carrier comprising:
a carrier body that includes a plurality of regions forming a pattern, the pattern coding an identification symbol, wherein:
the plurality of regions are volumes of the carrier body;
density values averaged over the volumes form the pattern;
at least two of the plurality of regions are spaced apart from each other or are stretched at least far enough such that at least one of (A) all straight lines that extend through voxels of both regions intersect at an angle of no more than 10°, and (B) one straight line through the centroid of the regions relative to the carrier is fixed with an accuracy of better than 5°; and
the density values averaged over the volumes differ from a density value of surrounding areas of the carrier body that has been determined by computed tomography.

10. The carrier of claim 9, wherein the at least two of the plurality of regions are spaced apart from each other or are stretched at least far enough such that all straight lines that extend through voxels of both regions intersect at an angle of no more than 5°.

11. The carrier of claim 9, wherein the at least two of the plurality of regions are spaced apart from each other or are stretched at least far enough such that all straight lines that extend through voxels of both regions intersect at an angle of no more than 1°.

12. The carrier of claim 9, wherein the at least two of the plurality of regions are spaced apart from each other or are stretched at least far enough such that one straight line through the centroid of the regions relative to the carrier is fixed with an accuracy of better than 1°.

13. The carrier of claim 9, wherein at least three selected regions of the plurality of regions have averaged CT density values that contrast with the density of the adjoining carrier body as determined by computed tomography, and are arranged such that one of the three regions is not located on a straight line running through the other two of the three regions.

14. The carrier of claim 13, wherein volume centroids of the three regions form a triangle.

15. The carrier of claim 14, wherein each angle of the triangle is at least 15°.

16. The carrier of claim 14, wherein each angle of the triangle is at least 30°.

17. The carrier of claim 9, wherein the volumes of all the plurality of regions are at least partially solidly enclosed within the carrier body.

18. The carrier of claim 9, wherein the volumes of all the plurality of regions are completely solidly enclosed within the carrier body.

19. The carrier of claim 9, wherein the carrier body includes at least one of:
  at least one pallet with regions arranged near or on the center of a thickness of a base surface thereof;
  at least one pallet stack having at least one pallet, with each pallet of the stack being coded by a pattern indicating whether a further plane is present;
  columns that are provided with regions associated with the pattern; and
  a body that is adapted to a workpiece contour in which the regions associated with the pattern code a workpiece that is to be placed on it and are neither collinear nor coplanar.

20. The carrier of claim 9, wherein at least a part of the carrier body that is provided with the pattern made from the plurality of regions is produced by way of three-dimensional printing with areas corresponding to the regions at least one of: (a) being left free, (b) being formed as foam-like cavities, (c) have densities increased by inserted third bodies, by being formed with varying printing parameter, or by a materiel used to form or fill the regions.

21. The carrier of claim 9, wherein the volumes of the regions comprise at least 5×5×5 voxels, with voxel sizes of >3 mm×3 mm×3 mm.

* * * * *